(12) United States Patent
Geller

(10) Patent No.: US 8,409,295 B2
(45) Date of Patent: Apr. 2, 2013

(54) METHOD AND APPARATUS FOR REPLACING A FEMORAL COMPONENT OF A HIP JOINT

(76) Inventor: David S. Geller, New York, NY (US)

( * ) Notice: Subject to any disclaimer, the term of this patent is extended or adjusted under 35 U.S.C. 154(b) by 0 days.

(21) Appl. No.: 12/861,712

(22) Filed: Aug. 23, 2010

(65) Prior Publication Data

US 2011/0077747 A1    Mar. 31, 2011

Related U.S. Application Data

(60) Provisional application No. 61/274,811, filed on Aug. 21, 2009.

(51) Int. Cl.
*A61F 2/32* (2006.01)
(52) U.S. Cl. .................................... 623/22.42
(58) Field of Classification Search ..... 623/22.11–23.38
See application file for complete search history.

(56) References Cited

U.S. PATENT DOCUMENTS

| | | | |
|---|---|---|---|
| 2,490,364 A | 12/1949 | Livingston | |
| 3,024,785 A | 3/1962 | Martin | |
| 3,760,802 A | 9/1973 | Fischer et al. | |
| 3,779,239 A | 12/1973 | Fischer et al. | |
| 3,846,846 A | 11/1974 | Fischer | |
| 4,091,806 A | 5/1978 | Aginsky | |
| 4,520,511 A * | 6/1985 | Gianezio et al. | 623/22.46 |
| 4,756,711 A | 7/1988 | Mai et al. | |
| 4,911,722 A | 3/1990 | Crespy | |
| 4,936,863 A * | 6/1990 | Hofmann | 623/23.26 |
| 5,702,481 A | 12/1997 | Lin | |
| 6,355,069 B1 | 3/2002 | DeCarlo, Jr. et al. | |
| 7,044,977 B2 | 5/2006 | Ferree | |
| 2004/0019383 A1 | 1/2004 | Beguec | |
| 2004/0267373 A1 * | 12/2004 | Dwyer et al. | 623/22.12 |
| 2008/0039950 A1 | 2/2008 | Splieth et al. | |

* cited by examiner

*Primary Examiner* — David Isabella
*Assistant Examiner* — Ann Schillinger
(74) *Attorney, Agent, or Firm* — Pandiscio & Pandiscio

(57) ABSTRACT

A prosthesis comprising an elongated stem for disposition within a cavity formed in a bone, the stem comprising a longitudinal axis and being configured for incremental controlled expansion laterally of the longitudinal axis, whereby to secure the prosthesis within the cavity by means of a press-fit with the surrounding bone.

23 Claims, 16 Drawing Sheets

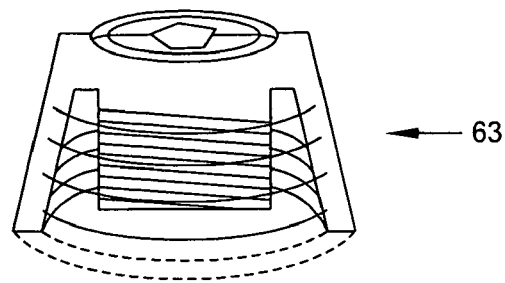
FIG. 21
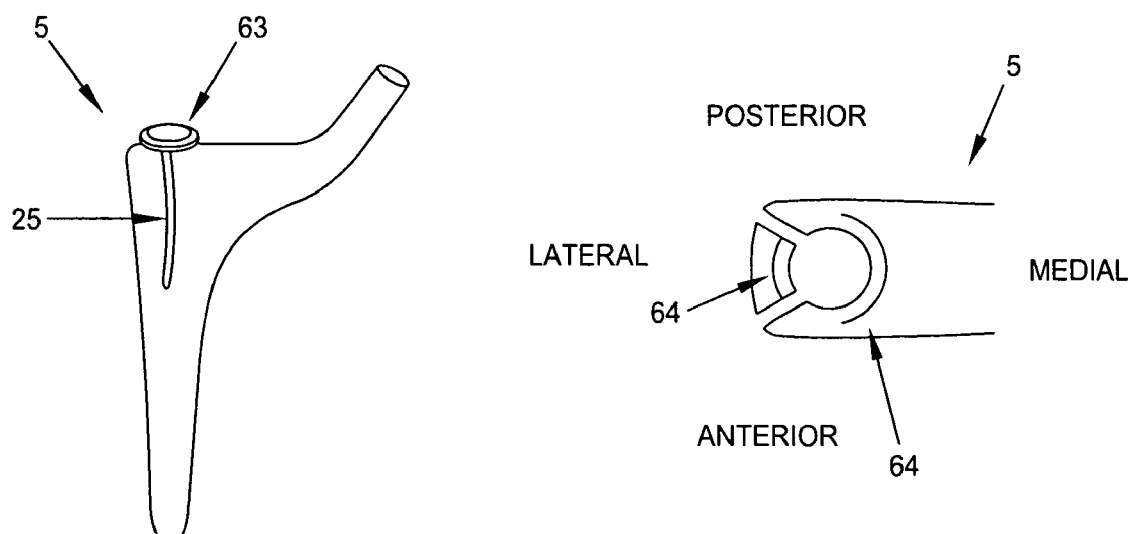
FIG. 23
FIG. 22

METHOD AND APPARATUS FOR REPLACING A FEMORAL COMPONENT OF A HIP JOINT

REFERENCE TO PENDING PRIOR PATENT APPLICATION

This patent application claims benefit of prior U.S. Provisional Patent Application Ser. No. 61/274,811, filed Aug. 21, 2009 by David S. Geller for OPS™ FRACTURE FIXATION SYSTEM, which patent application is hereby incorporated herein by reference.

FIELD OF THE INVENTION

This invention relates to medical apparatus and procedures in general, and more particularly to medical apparatus and procedures for replacing a femoral component of a hip joint.

BACKGROUND OF THE INVENTION

The hip joint is a ball-and-socket joint which movably connects the leg to the torso. The hip joint generally comprises a femoral component (i.e., the neck and ball at the top end of the femur) and an acetabular component (i.e., the acetabular cup formed in the pelvis).

In many situations, a femoral component of a hip joint may need to be replaced by a prosthetic device. By way of example but not limitation, a femoral component of a hip joint may need to be replaced by a prosthetic device because of injury (e.g., a fracture of the femoral neck), degenerative disease (e.g., osteoarthritis, rheumatoid arthritis, post-traumatic arthritis, avascular necrosis of the femoral head, etc.), developmental pathologies (e.g., Perthes disease, developmental or congenital hip dysplasia, etc.), etc.

Such replacement of a femoral component of a hip joint with a prosthetic device typically includes surgical removal (or "resection") of the compromised femoral neck and head, followed by reconstruction using a femoral prosthesis, as will hereinafter be dismissed. In many cases, the acetabular cup may also be replaced by a prosthetic device. Where both the femoral component and the acetabular component are replaced by prosthetic devices, the procedure is commonly referred to as a "total hip replacement" (THR), or a "total hip arthroplasty" (THA), or a "bipolar hip reconstruction"; and where only the femoral component is replaced by a prosthetic device, the procedure is commonly referred to as a "hemiarthroplasty", or a "unipolar hip reconstruction". In any case, the surgical goals of replacing the injured and/or diseased bone and cartilage surfaces with a prosthetic device is to reduce pain, improve range of motion, improve weight-bearing ability, increase mobility and, in turn, decrease the risk of recumbency-related complications.

The femoral prosthesis generally comprises a femoral stem, a femoral head (or "ball"), and a femoral neck. The femoral stem is received within the intramedullary space of the proximal femur. The femoral head is designed to articulate within the acetabular component of the hip joint (i.e., in either a prosthetic acetabular cup or the native acetabular cup). The femoral head is connected to the femoral stem by the femoral neck, and the femoral head is typically locked to the femoral neck via a Morse taper mechanism. The femoral neck is typically formed integral with the femoral stem, although in some cases they may comprise separate components which are united during surgery.

The femoral stem is generally constructed from a high-strength metal alloy or stainless steel, and its outer surface is often treated and/or configured so as to promote bony ingrowth, bony ongrowth, or bony interdigitation.

The femoral stem can be fixed within the intramedullary space of the proximal femur by either using bone cement (e.g., methylmethacrylate) or in a cementless press-fit manner (hereinafter referred to simply as "press-fit").

The present invention is directed to press-fit femoral stems.

Press-fit implantation is commonly referred to as a "biologic reconstruction" in the sense that the host bone will eventually grow into, and/or onto, the femoral stem's outer surface over a period of weeks to months. In the immediate post-operative period, and until such time that biologic reconstruction (i.e., bone growth) can provide bony implant security, the stability of the femoral stem is dependent upon radially directed hoop-stresses which are created when the implant is forcefully wedged into the intramedullary space. In this respect it should be appreciated that the stability of the femoral stem is vital in order to ensure long-term prosthetic functionality and for maintaining equal leg length (relative to the contralateral limb). Early loosening of the femoral stem, and/or selecting an under-sized femoral stem, may lead to subsidence (or "sinking") of the implant further within the intramedullary space of the proximal femur, thereby resulting in leg length inequality, altered hip biomechanics, and gait abnormality. Early loosening of the femoral stem is also associated with pain and, frequently, with the need for subsequent revision hip surgery.

Conversely, an over-aggressive impaction of the femoral stem (i.e., selecting an over-sized femoral stem) may result in exceeding the hoop-stress capacity of the proximal femoral bone, thereby resulting in a fracture of the femoral bone. Such an occurrence will, at a minimum, require additional surgical attention and may also require additional weight-bearing restrictions for the patient. If unrecognized, this fracturing of the bone may also result in post-operative subsidence of the femoral stem (and hence sub-optimal function of the joint and substantial pain for the patient) and may necessitate revision surgery.

In addition to the foregoing, stress shielding is a phenomenon where normal, physiological stress forces travel unequally across an implant and, in so doing, may bypass a region of bone such as the proximal femur. Since substantial bone density and substantial bone strength are enhanced by the presence of stress, the occurrence of stress shielding can result in decreased bone density and decreased bone strength in the area of the bone which is stress shielded. This phenomenon, commonly referred to as Wolff's law, is well known by those skilled in the art. Because of this phenomenon, it is generally desirable to minimize stress shielding when deploying a femoral stem in a bone, so as to maintain bone strength/integrity in the region adjacent to the implant and thereby avoid fractures through the region.

Current press-fit femoral stem designs typically comprise either (i) a "proximally coated" (or a "proximally porous-coated") stem, or (ii) a "fully coated" (or a "fully porous-coated") stem.

The "proximally coated" stem design permits biologic fixation via bone ingrowth, or ongrowth, along the more proximal region of the stem. The proximally coated stem design benefits from minimizing bone loss secondary to stress shielding, however, the initial stem stability is completely dependent upon the hoop-stresses created when the implant is forcefully wedged into the intramedullary space of the proximal femur.

Conversely, the "fully coated" stem design promotes bony ingrowth, or ongrowth, along the entire length of the femoral stem. The fully coated stem design is intended to provide diaphyseal (i.e., more distal) bone fixation and does not depend upon the hoop-stresses resulting from wedging the bone into the more proximal region of the femur. This fully coated stem design establishes an initial wedging, or "scratch fit", along the length of the femoral diaphysis. The fully coated stem design frequently includes a collar, which prevents implant subsidence and serves to mark the desired longitudinal implant height within the intramedullary space of the proximal femur. The fully coated stem design benefits from excellent initial and long term fixation but, conversely, can be associated with stress shielding of the proximal femur. In addition, removal of this type of implant, as may be required in certain situations such as infection, can be more technically challenging than with a proximally coated stem design and can, in some instances, result in a greater degree of iatrogenic bone loss.

Thus, there is a need in the art for a new femoral prosthesis which maximizes the benefits of press-fit technology while minimizing the disadvantages and inadequacies of the prior art previously described.

SUMMARY OF THE INVENTION

These and other objects of the present invention are addressed by the provision and use of a novel femoral prosthesis.

More particularly, the present invention comprises the provision and use of a novel femoral prosthesis which comprises a femoral stem which utilizes a novel proximally coated stem design which enables incremental controlled press-fit implantation of the femoral stem. As a result, the femoral implant permits accurate, controlled and adjustable sizing of the implant, whereby to provide secure implant fixation while preventing implant subsidence, stress shielding, and proximal femoral function. Thus, the novel femoral implant essentially permits press-fit primary coated stem implantation via adjustable pressurization of the proximal femur. The invention may sometimes hereinafter be termed or referred to as the "Optimally Pressurized Stem (OPS) System", and/or the "OPS fracture fixation system", and/or the "OPS system", etc.

In one preferred form of the present invention, there is provided a novel femoral prosthesis which comprises a press-fit femoral stem having a longitudinally-extending slit formed therein, wherein the longitudinally-extending slit opens on the proximal surface of the femoral stem and extends distally along the femoral stem, thereby permitting optimal expansion of the femoral stem following implantation, so as to ensure improved fit with the host bone and minimization of stress shielding of the adjacent native bone.

In one preferred form of the present invention, the longitudinally-extending slit crosses the entire anterior-to-posterior dimension of the implant ("a sagittal slit"), thereby allowing for expansion of the implant in a medial-to-lateral direction.

In one preferred form of the present invention, the femoral stem also includes an expansion hole extending distally from the proximal surface of the femoral stem, and longitudinally aligned either symmetrically or asymmetrically with respect to the longitudinally-extending slit, and which extends for either a portion of, or all of, the length of the longitudinally-extending slit. The distal portion of the expansion hole is preferably threaded and maintains an equal diameter throughout the threaded portion of the expansion hole. The proximal portion of the expansion hole is preferably smooth and is tapered in the coronal plane, whereby it is wider proximally and narrows distally.

In one preferred form of the present invention, there is also provided an expansion bolt, which is distally threaded and proximally smooth and sized to be received within the expansion hole. The threaded portion of the expansion bolt maintains a constant diameter over its entire length, while the smooth portion of the expansion bolt is tapered, with the proximal aspect of the smooth portion being wider and the distal aspect of the smooth portion being narrower. The expansion bolt may also have a smaller threaded hole which would allow for engagement of a secondary locking set screw.

The invention provides that the threaded portion of the expansion hole and the threaded portion of the expansion bolt correspond with regard to core diameter, thread size, and thread pitch. The smooth tapered portion of the expansion hole and the smooth tapered portion of the expansion bolt are sized, in diameter and taper, such that advancement of the expansion bolt within the expansion hole results in expansion of the implant in a medial-to-lateral direction. To this end, it may be necessary to modify the degree of the bolt taper, the length of the bolt taper, and/or the shape of the smooth tapered portion of the expansion bolt in a manner consistent with the desired effect so as to provide controlled and reliable expansion of the femoral stem when the expansion bolt is advanced down the expansion hole. The final position of the expansion bolt may sit proud relative to the femoral stem, or it may sit recessed within the expansion hole, and may depend to some extent upon how far the expansion bolt is advanced into the expansion hole of the femoral stem and how much expansion of the femoral stem is required.

The present invention also includes an expansion driver for driving the expansion bolt. The expansion driver can be in the form of a torque driver with a pre-set limit so as to prevent over-expansion of the implant (and hence prevents generation of excessive internal hoop stresses on the host bone). Alternatively, the expansion driver can be linked to a force meter whereby inherent resistance to advancement can be measured and resistance from surrounding bone can be determined. The spirit of the instrument and the system is understood to be a means whereby excessive force generation is prevented while incrementally and reproducibly applying post-implant press-fit stability via lateral implant expansion.

As noted above, the longitudinally-extending sagittal slit preferably extends across the entire anterior-to-posterior dimension of the implant. Alternatively, the longitudinally-extending sagittal slit may extend only part way across the implant, e.g., from the anterior surface of the implant to the expansion hole, or from the posterior surface of the implant to the expansion hole.

And/or the longitudinally-extending sagittal slit may be replaced by a plurality of parallel longitudinally-extending sagittal slits.

In one preferred form of the present invention, the aforementioned longitudinally-extending sagittal slit can be combined with a second longitudinally-extending slit which starts at the expansion hole and extends laterally in a medial-to-lateral direction ("a coronal slit"). The coronal slit allows for expansion in an anterior-to-posterior direction. Thus, the combination of a sagittal slit and a coronal slit allows for expansion of the femoral stem in both a medial-to-lateral direction and in an anterior-to-posterior direction and may aid in achieving optimal press-fit stability.

The longitudinally-extending coronal slit may extend medially of the expansion hole, or laterally of the expansion hole, or both.

And/or the longitudinally-extending coronal slit may be replaced by a plurality of parallel longitudinally-extending coronal slits.

In one preferred construction, the aforementioned longitudinally-extending sagittal slit and the aforementioned coronal slit are replaced by one or more longitudinally-extending slits that extend at a non-perpendicular angle to both the sagittal plane and the coronal plane.

The longitudinally-extending slits may also take on more complex geometric configurations, e.g., they may start in the sagittal plane and migrate laterally as they extend distally so as to end in the coronal plane—this three-dimensional shift relative to proximal/distal location can provide a large surface area for expansion while minimizing the risk of implant or bone failure along the length of the longitudinally-extending slit.

Additional slit configurations, which will be apparent to those skilled in the art in view of the present disclosure, may be utilized in order facilitate incrementally controlled expansion of the femoral stem.

In one embodiment of the present invention, the distal aspect of the longitudinally-extending slit may terminate abruptly, or it may terminate in a tapered or graduated manner, or it may terminate in an unequal or asymmetric manner, with the anterior aspect of the slit terminating at a different longitudinal location than the posterior aspect of the slit. The present invention further provides that the terminal or distal extent of the longitudinally-extending slit may terminate in another geometrically configured manner which includes, but is not limited to, a circular hole, an oval or oblong hole, or an otherwise rounded hole, the purpose of which is to minimize stress and implant fracture at this implant location, i.e., a "stress relief hole" or, more simply, a "relief hole". Similarly, any additional slit configurations including, but not limited to, slits in the sagittal plane or the coronal plane may also terminate in a geometric shape or design (e.g., a circle, an oval, a rectilinear shape, a combination of shapes, etc.) which distributes stress over a larger area and which serves to minimize the forces and risk of fracture at the slit end.

The present invention may also include a locking set screw intended to prevent or protect against backing-out or loosening of the expansion bolt. The locking set screw is intended to pass through a bore in the femoral stem and engage the expansion bolt so as to lock the expansion bolt in place.

In one form of the present invention, the femoral stem may or may not include a collar, which is commonly defined as a prominence or extension along the medial aspect of the femoral stem, at the junction of the femoral neck and the metaphyseal body of the femoral stem. The collar typically rests upon the medial femoral bone known as the calcar, and serves to further protect against subsidence of the femoral stem. Unlike prior designs where the final press-fit stability is dependent upon sinking or advancing the stem further distally within the intramedullary canal of the femur, the present invention permits post-implantation expansion of the femoral stem. The present invention also serves to uncouple two previously-linked goals, namely, the requirement for proper press-fit rotational stability and the requirement of proper and stable implant height. For these reasons, incorporation of a medial collar does not prohibit final expansion and press-fit implantation and further protects against subsidence.

The present invention further provides for the incorporation of a neutralization (or "locking") device (e.g., a cap or bar or screw, etc.), the purpose of which is to offset or neutralize forces passed across the slit (or slits) and measured at a variable level medial to the slit. The neutralization (or "locking") device (e.g., cap or bar or screw, etc.) is intended to engage the proximal aspect of the femoral stem in a manner which crosses the longitudinally-extending slit and which serves to bridge the more medial aspect and the more lateral aspect of the proximal femoral stem, with the intent to limit or neutralize bending and stress at the most distal extent of the longitudinally-extending slit.

In one form of the invention, there is provided a prosthesis comprising an elongated stem for disposition within a cavity formed in a bone, the stem comprising a longitudinal axis and being configured for incremental controlled expansion laterally of the longitudinal axis, whereby to secure the prosthesis within the cavity by means of a press-fit with the surrounding bone.

In one form of the invention, there is provided a method for securing a prosthesis within a cavity formed in a bone, the method comprising:

providing a prosthesis comprising an elongated stem, the stem comprising a longitudinal axis and being configured for incremental controlled expansion laterally of the longitudinal axis;

inserting the prosthesis into the cavity; and expanding the prosthesis laterally of the longitudinal axis, whereby to secure the prosthesis within the cavity by means of a press-fit with the surrounding bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 12-17, 17A and 18-23 are schematic views showing various additional constructions for the present invention.

DEFINITIONS

Figure 1:
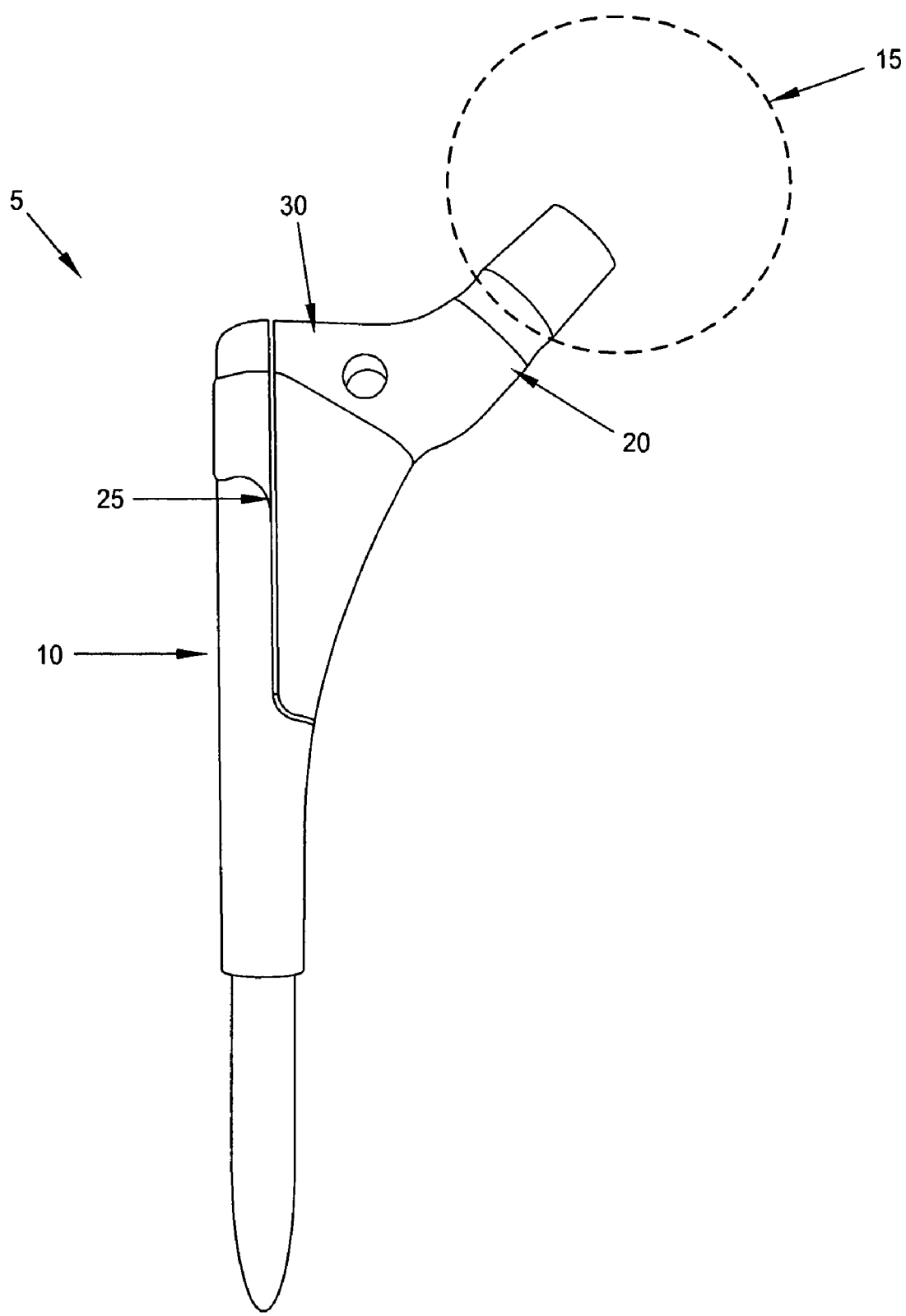
FIG. 1 is a schematic side view showing a femoral prosthesis formed in accordance with the present invention.

As used herein, the term "femoral stem" is intended to refer to a stainless steel or metal alloy prosthetic implant, or an implant made of another material, that allows for the transmission of force from the femur through the hip joint. It replaces native bone and cartilage, allowing for restoration of the hip joint. Preferably, but not necessarily, the femoral stem is formed integral with the femoral neck, which receives the femoral head, as discussed above.

As used herein, a "press-fit" femoral stem refers to any femoral stem that utilizes cementless technology and is implanted using a cementless technique. Such technology includes, but is not limited to, proximal porous coating structures, grit blasting, hydroxyapatite coatings (HA coatings), trabecular metal coatings, and/or any similar highly porous surfaces designed to promote proximal bone ingrowth or ongrowth.

As used herein, "press-fit" implantation or the "press-fit" technique refers to a method of inserting the femoral stem such that longitudinally-directed force is used to set the femoral stem in the femur. More particularly, with press-fit implantation, force is imparted (via mallet strikes) to the femoral stem via a stem inserter of the sort well known in the art. The resulting effect is distal migration of the femoral stem relative to the femur and, ultimately, the fitting or wedging of the femoral stem within the metaphyseal bone of the proximal femur.

As used herein, "hoop-stress" refers to the mechanical circumferential stress resulting from internal pressure of the femoral stem against the surrounding bone.

As used herein, femoral stem or implant "stability" refers to the maintenance of position of the femoral stem in all axes, including (i) longitudinal stability which would prevent translation parallel to the femur shaft axis, and (ii) rotational stability which would prevent rotation around the femoral shaft axis.

As used herein, femoral stem or implant "subsidence" refers to the slippage or movement of the implant from its original position along one or more axes (typically the longitudinal axis) over the course of time.

As used herein, a "fracture" refers to a crack in, a break in, or a disruption of, normal cortical bone continuity.

As used herein, implant "expansion" refers to the widening of the final implant once the implant is seated or inserted within the proximal femur. It refers to an increase in the medial-to-lateral distance of the proximal implant, and/or to an increase in the anterior-to-posterior distance of the proximal implant. It does not mean to imply that the implant is symmetrically expanding, e.g., in the manner of a balloon or a tire.

DETAILED DESCRIPTION OF THE PREFERRED EMBODIMENT

The present invention comprises the provision and use of a novel femoral prosthesis for replacing the femoral component of the hip joint.

More particularly, the present invention provides incremental controlled press-fit implantation of a femoral stem. As a result, the femoral implant permits accurate controlled sizing of the implant, whereby to provide secure implant fixation while preventing implant subsidence, stress shielding and proximal femoral fracture. Thus, the novel femoral implant essentially permits press-fit coated stem implantation via adjustable pressurization of the proximal femur.

Novel Femoral Prosthesis

Looking now at FIG. 1, there is shown a femoral prosthesis 5 which generally comprises a press-fit femoral stem 10, a femoral head (or "ball") 15, and a femoral neck 20. The femoral stem is received within the intramedullary space of the proximal femur. The femoral head is designed to articulate within the acetabular component of the hip joint (i.e., either a prosthetic acetabular cup or the native acetabular cup). The femoral head is connected to the femoral stem by the femoral neck, and the femoral head is typically locked to the femoral neck via a Morse taper mechanism. The femoral neck is typically formed integral with the femoral stem, although in some cases they may comprise separate components which are united during surgery.

In accordance with the present invention, the press-fit femoral stem 10 comprises a longitudinally-extending slit 25 formed therein. Longitudinally-extending slit 25 opens on proximal surface 30 of femoral stem 10 and stops intermediate the length of femoral stem 10, so as to provide a hinge between the bifurcated portions of the femoral stem. Longitudinally-extending slit 25 permits optimal expansion of the prosthesis after implantation, so as to ensure improved fit with the host bone and minimization of stress-shielding of the adjacent native bone. The length of longitudinally-extending slit 25 may be variable and will depend in part upon implant material and inherent material properties as well as implant-specific size and geometry.

In one preferred form of the present invention, longitudinally-extending slit 25 crosses the entire anterior-to-posterior dimension of the implant ("a sagittal slit"), thereby allowing for expansion of the implant in a medial-to-lateral direction.

Figure 2:
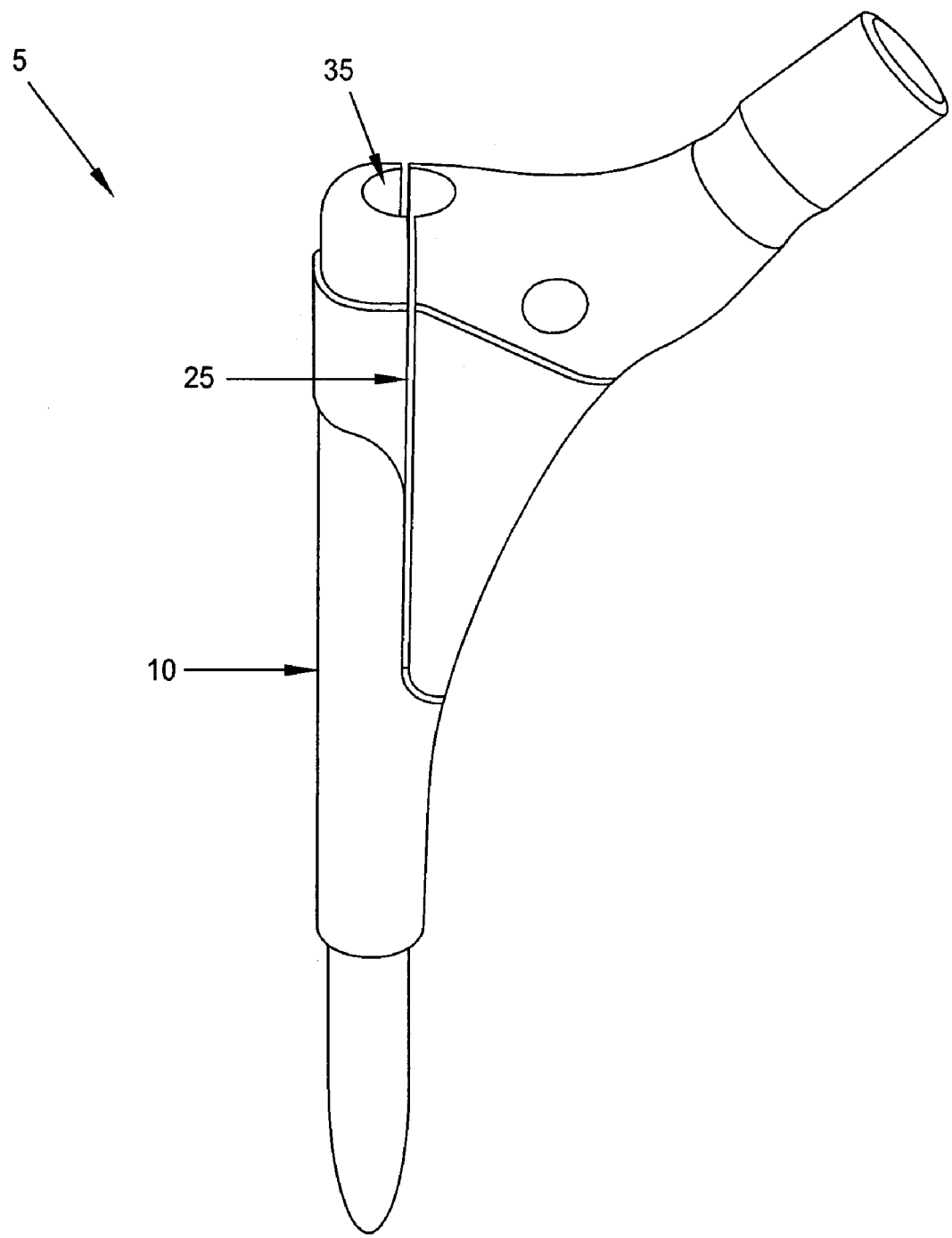
FIG. 2 is a schematic perspective view of the femoral prosthesis shown in FIG. 1.
Figure 3:
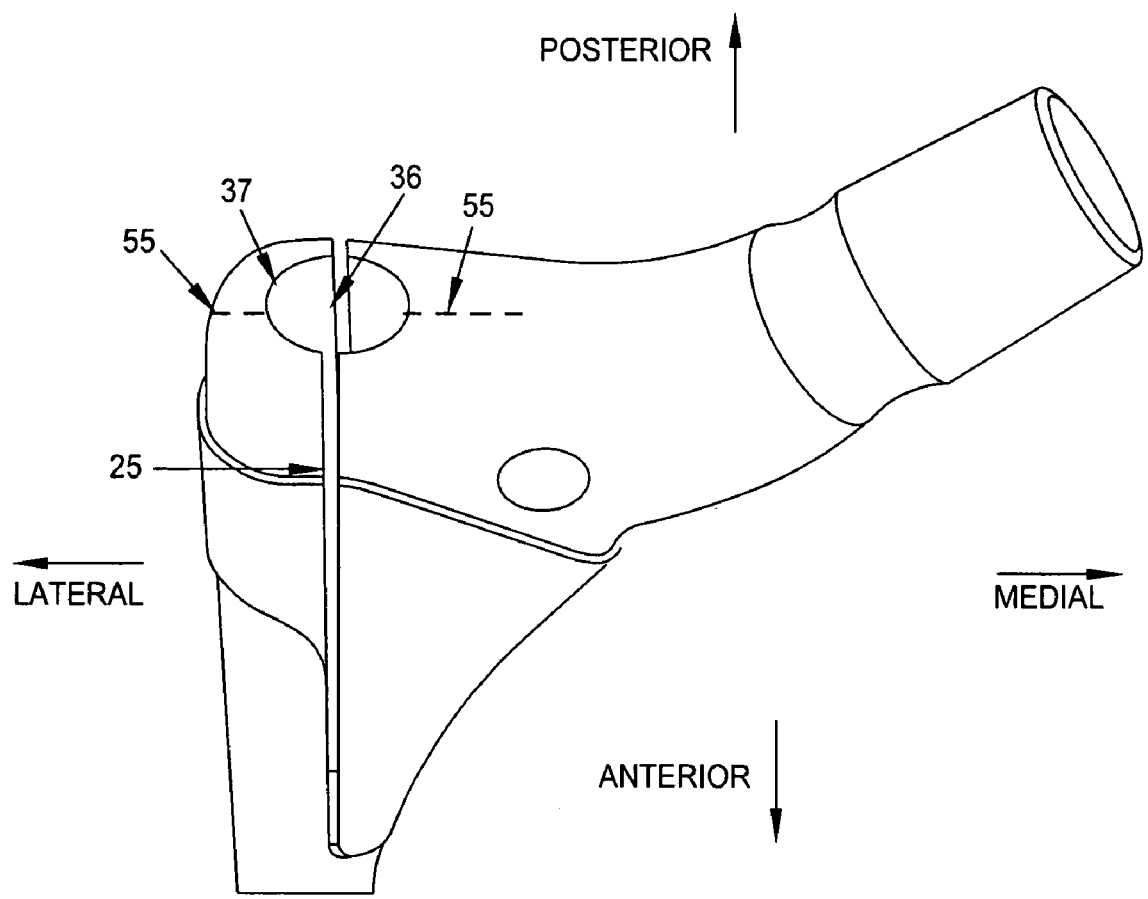
FIG. 3 is an enlarged perspective view of the femoral prosthesis shown in FIG. 2.

Looking now at FIGS. 2 and 3, femoral stem 10 includes an expansion hole 35 within the proximal portion of the femoral stem 10, which is either symmetrically or asymmetrically centered over the longitudinally-extending slit 25, and which extends for either part of or all of the length of the longitudinally-extending slit 25. Expansion hole 35 comprises a distal portion 36 and a proximal portion 37. The distal portion 36 of expansion hole 35 has a constant diameter and is threaded. The proximal portion 37 of expansion hole 35 (i.e., the portion adjacent to proximal surface 30) is smooth and tapered in the coronal plane, whereby it is wider proximally and more narrow distally.

Figure 4:
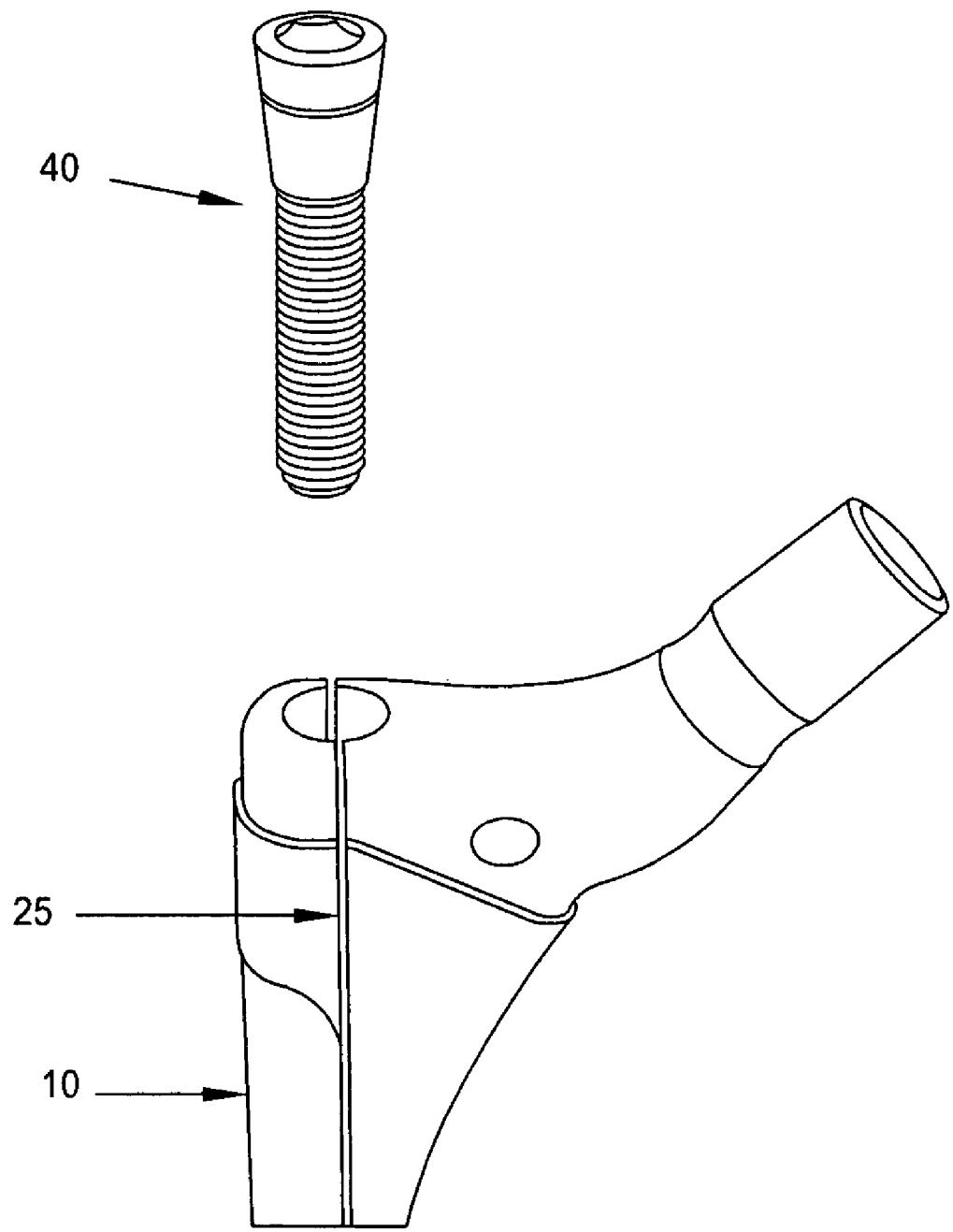
FIG. 4 is a schematic view showing the femoral prosthesis of FIG. 3 and an expansion bolt for use with the same.
Figure 5:
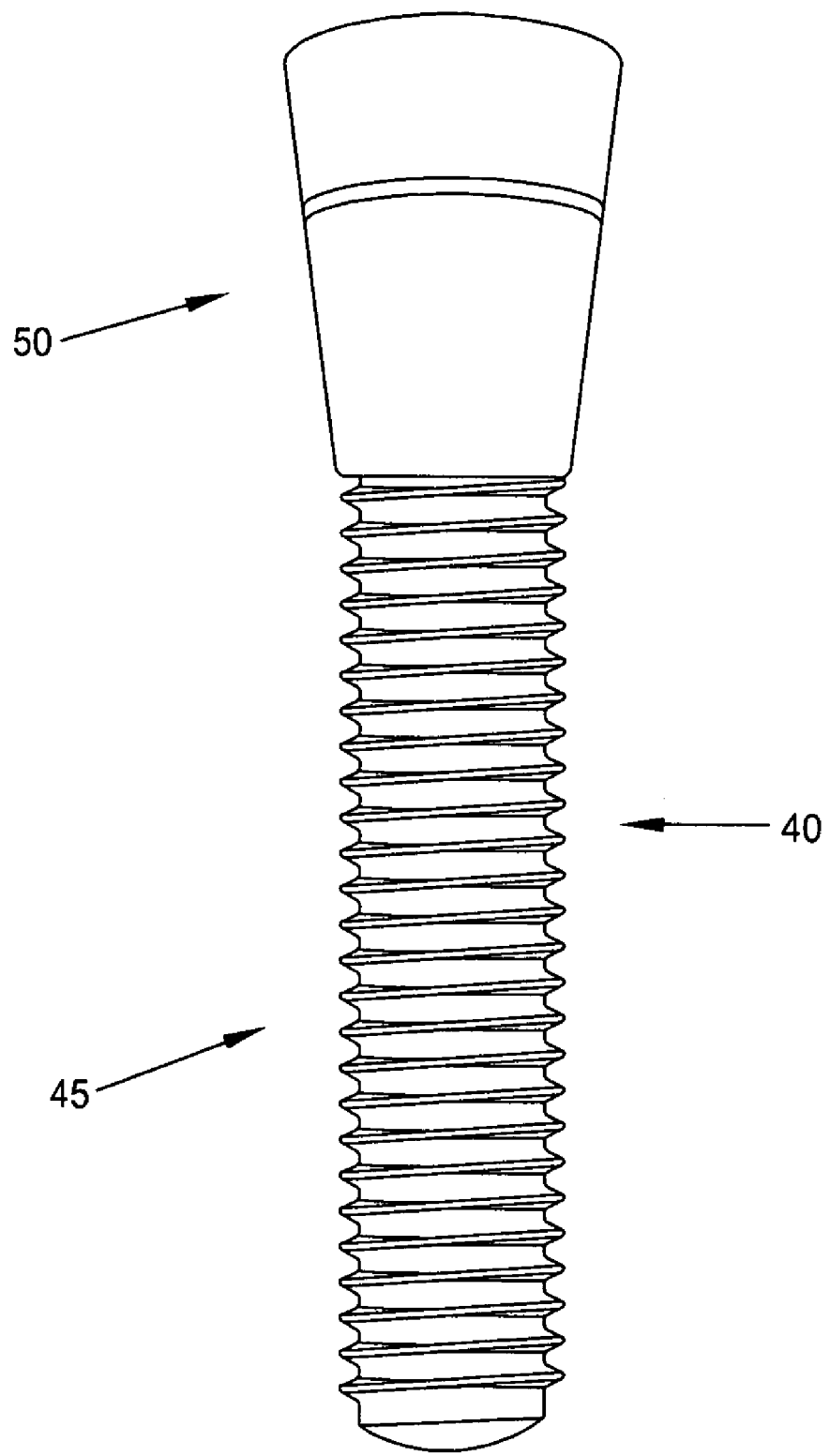
FIGS. 5 and 6 are schematic views showing details of the expansion bolt of FIG. 4.
Figure 6:
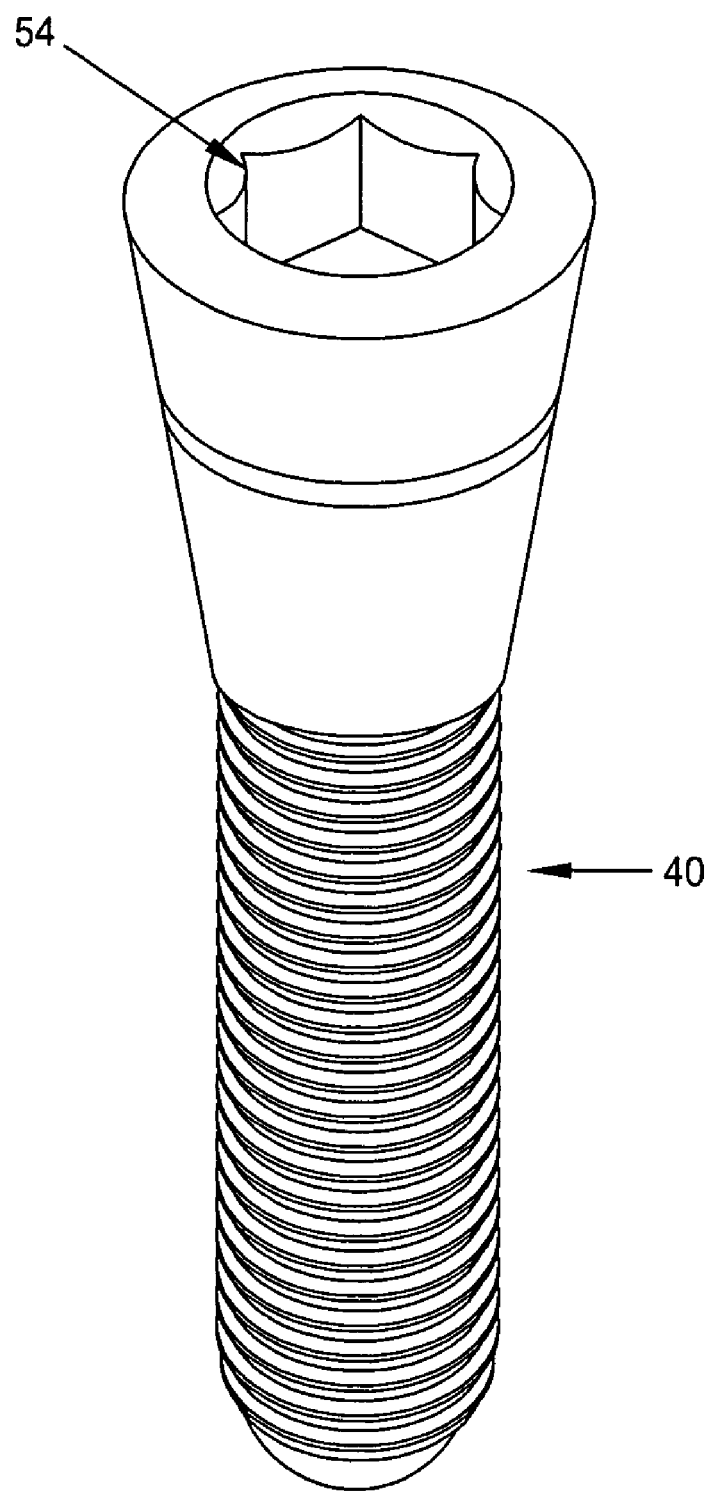

Looking next at FIGS. 4-6, femoral prosthesis 5 also includes an expansion bolt 40. Expansion bolt 40 comprises a distal portion 45 and a proximal portion 50. Distal portion 45 has a constant diameter and is threaded. Proximal portion 50 is tapered and has a smooth outer surface. Proximal portion 50 includes a hex-shaped recess 54 (FIG. 6) at its proximal end for receiving a driver 53 (FIGS. 9 and 11), whereby to turn expansion bolt 40 as will hereinafter be discussed.

Figure 7:
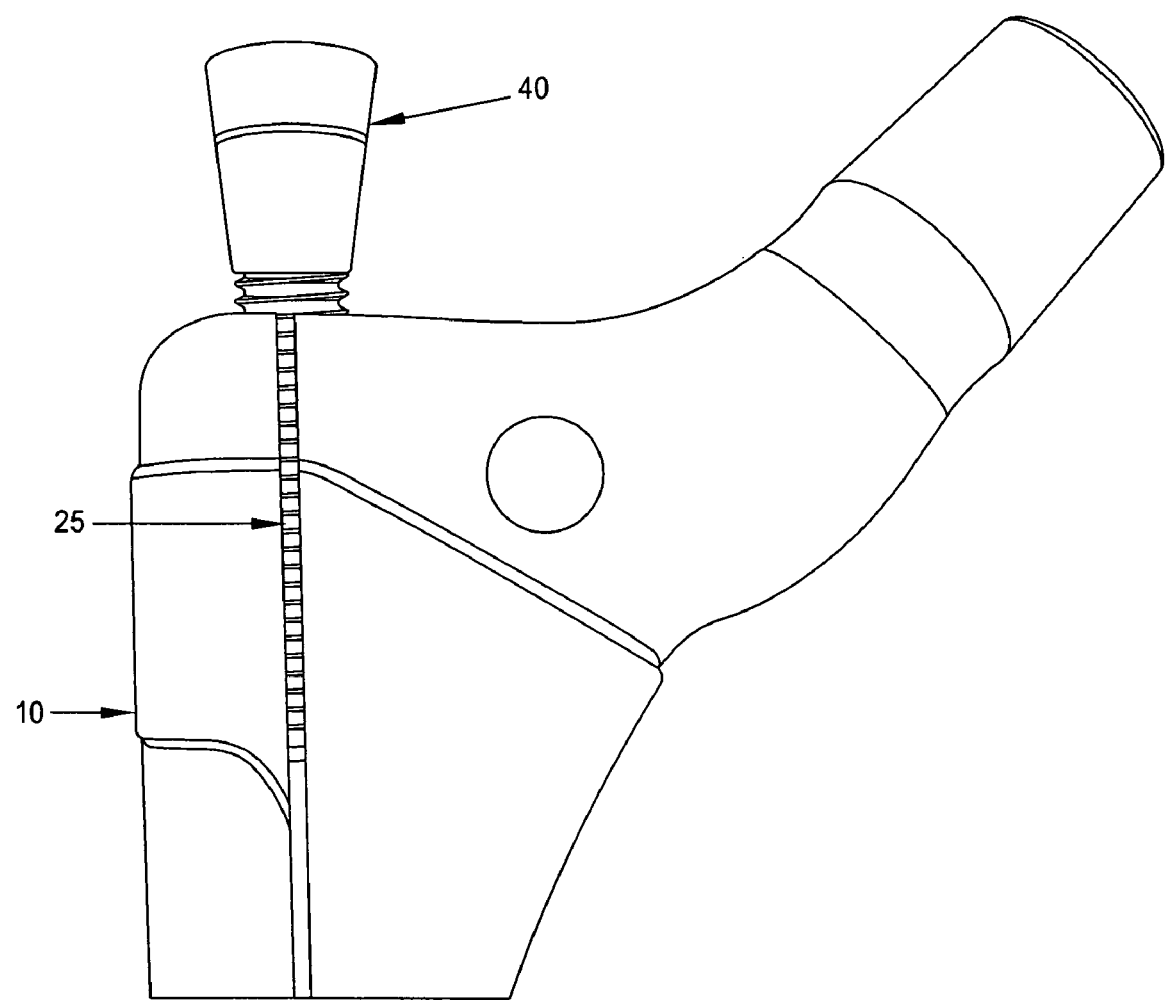
FIGS. 7-11 are schematic views showing the expansion bolt of FIGS. 5 and 6 being used to adjust the configuration of the femoral prosthesis of FIG. 1.
Figure 8:
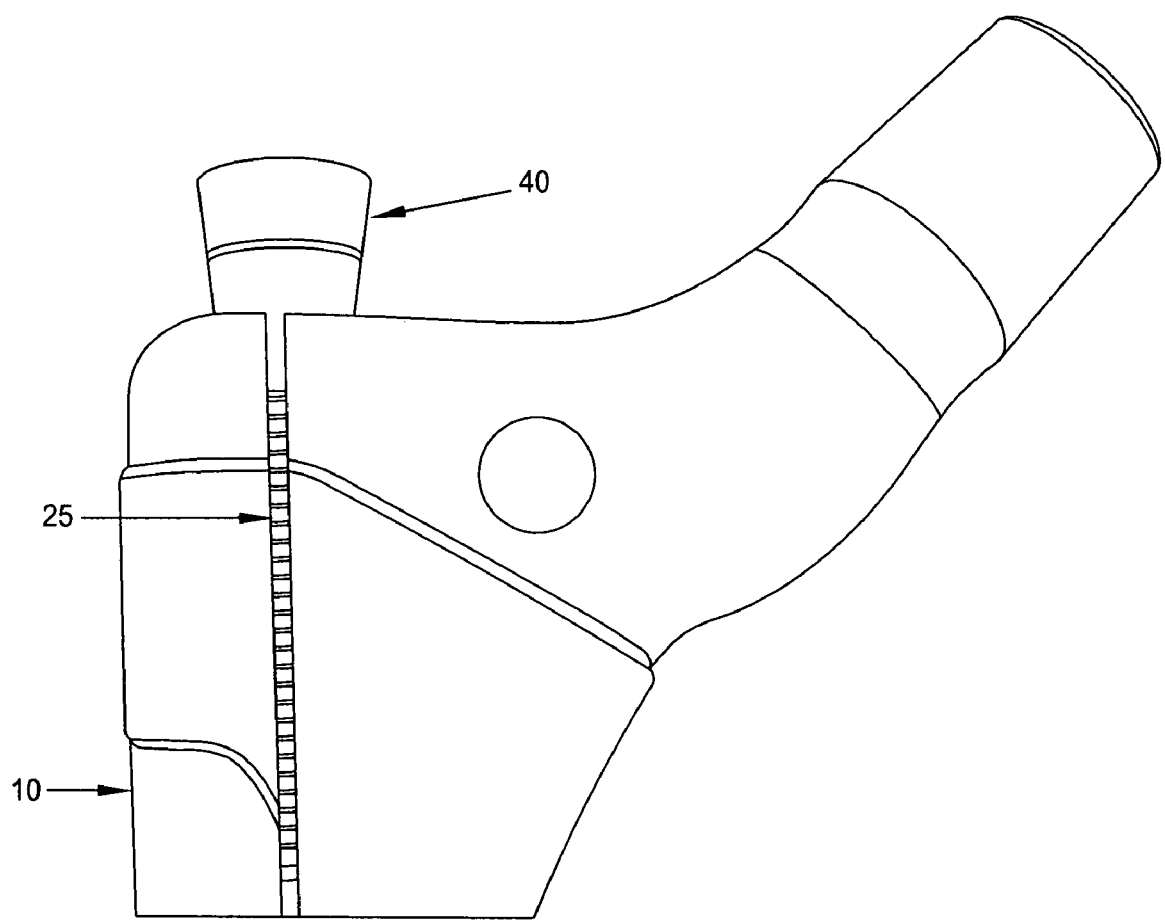
Figure 9:
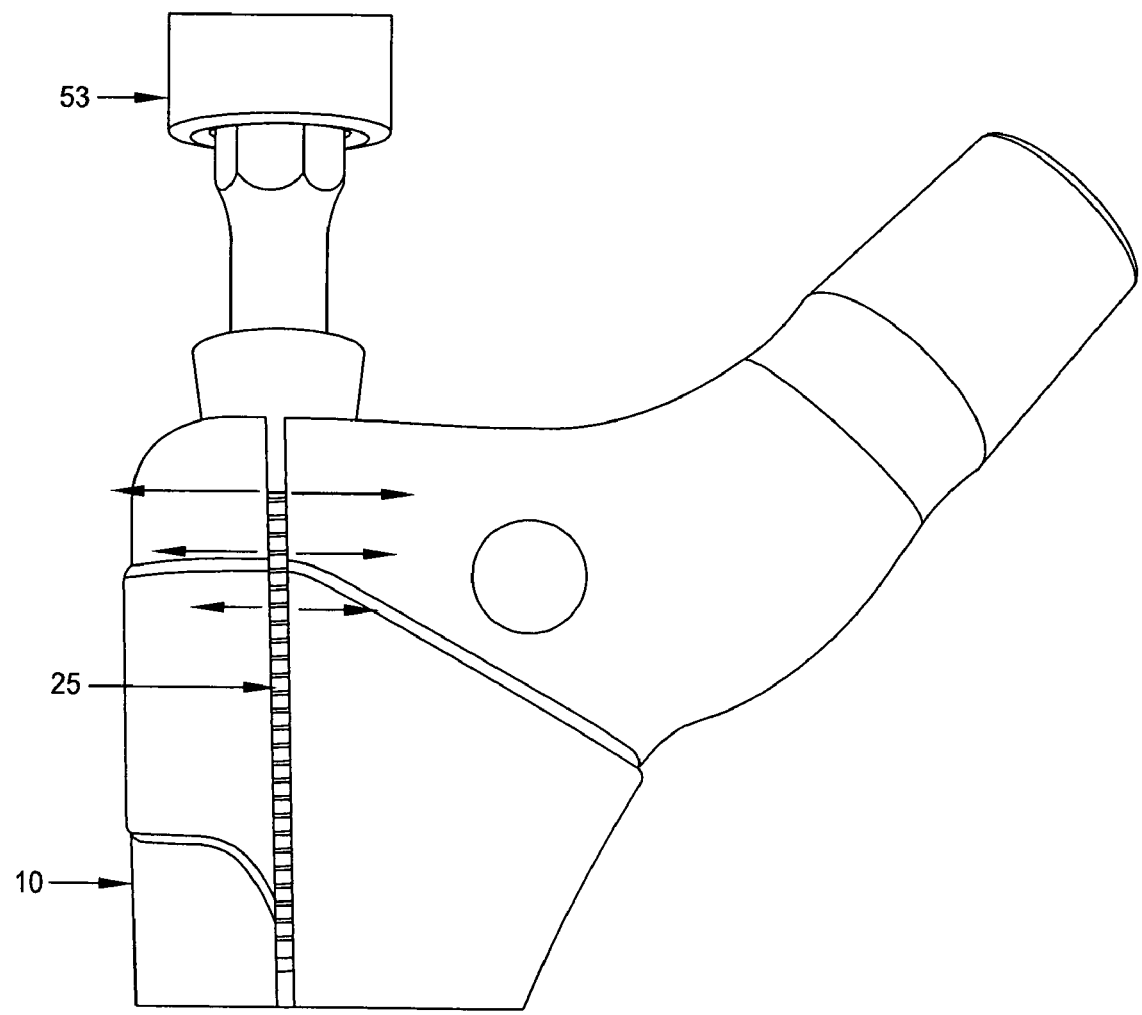
Figure 10:
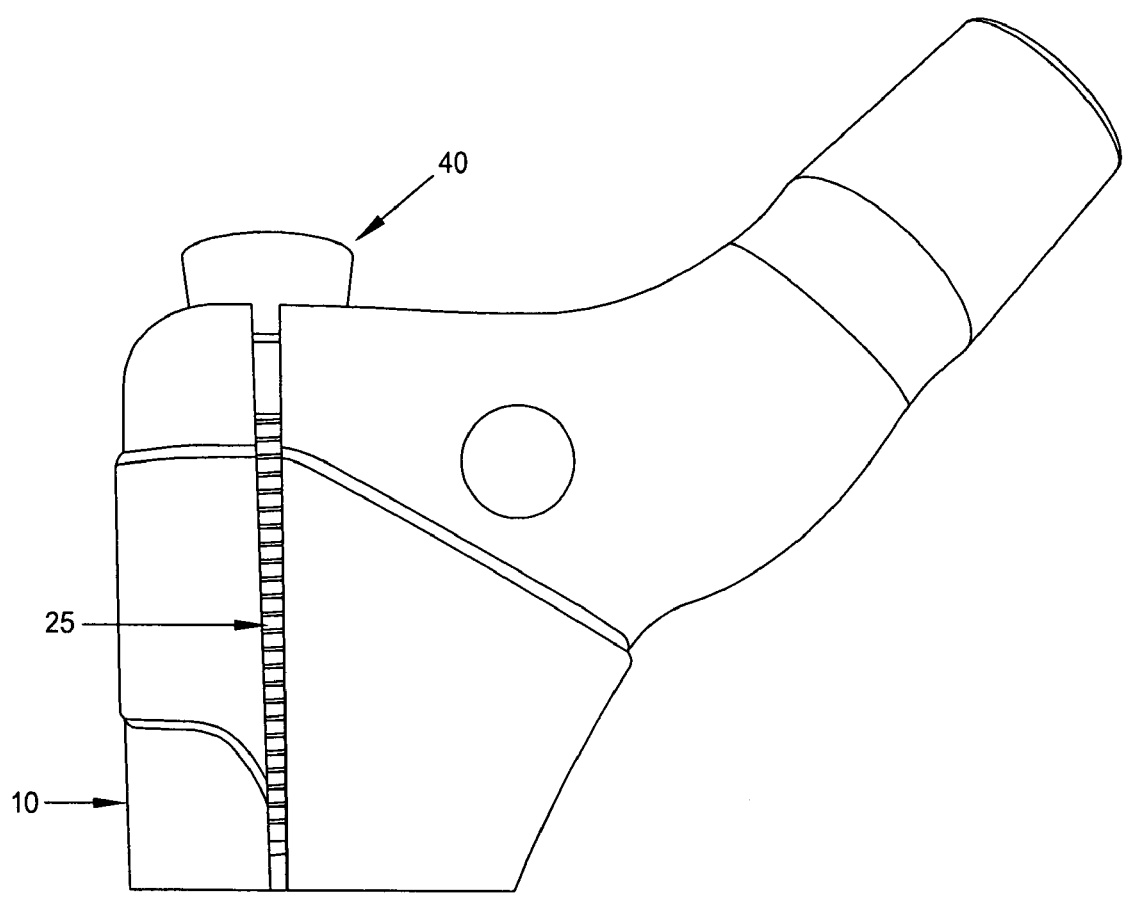
Figure 11:
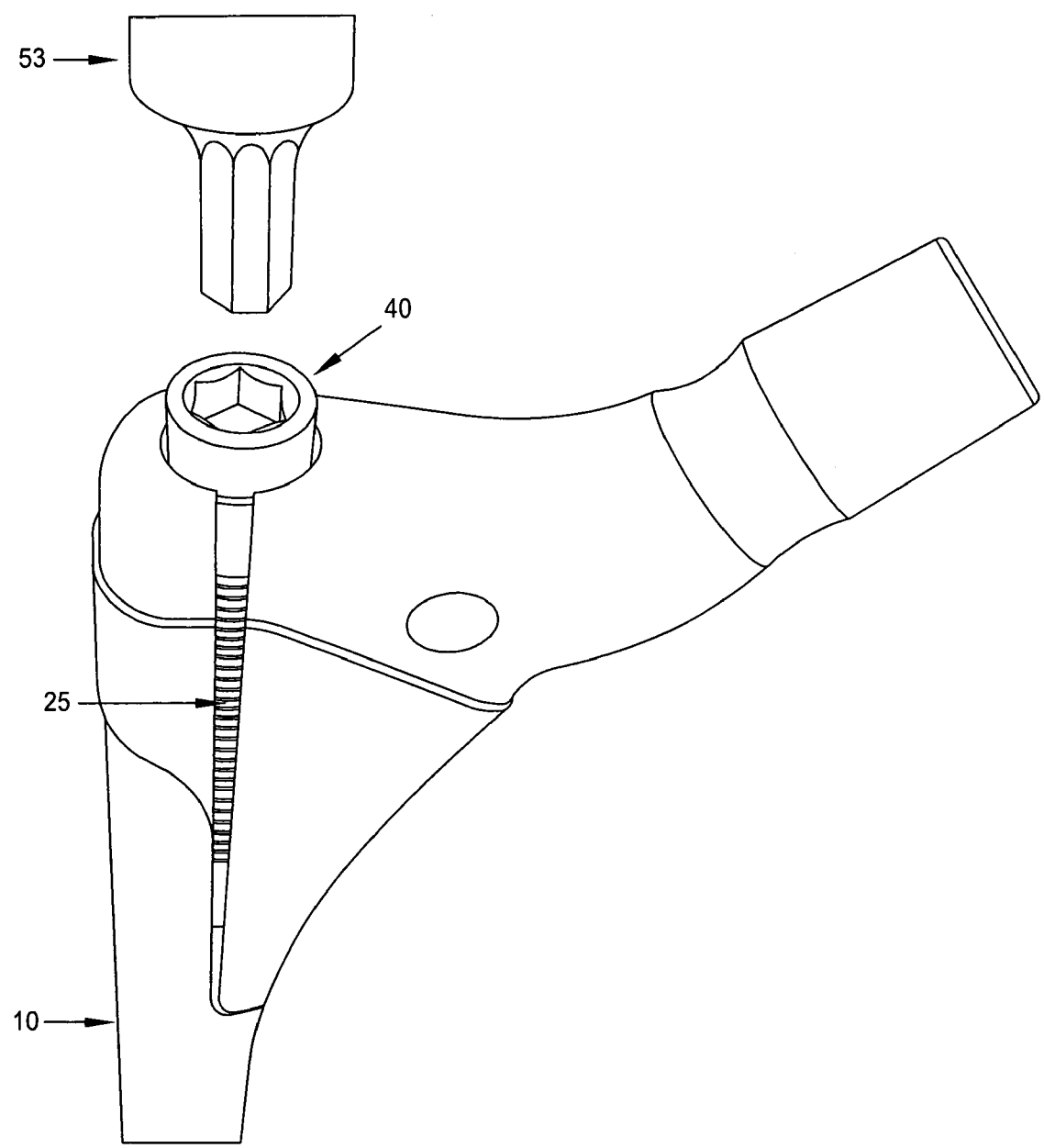

In accordance with the present invention, the threaded portion of expansion hole 35 and the threaded portion of expansion bolt 40 correspond with one another with regard to core diameter, thread size, and thread pitch. Also in accordance with the present invention, the smooth tapered portion of expansion hole 35 and the smooth tapered portion of expansion bolt 40 correspond with one another with regard to diameter and taper such that advancement of expansion bolt 40 within expansion hole 35 results in expansion of the femoral stem in a medial-to-lateral direction. See FIGS. 7-10, wherein FIG. 7 shows the threaded portion of expansion bolt 40 engaging the threaded portion of expansion hole 35, and wherein there is no engagement of the proximal portion of expansion bolt 40 and therefore no expansion; wherein FIG. 8. shows the threaded portion of expansion bolt 40 moving distally within expansion hole 35, and the proximal portion of expansion bolt 40 beginning to engage the femoral stem; wherein FIG. 9 shows expansion of the femoral stem in a medial-to-lateral direction, wherein advancement of the expansion bolt may be controlled in a finely tuned manner using a torque wrench to limit excessive force; and wherein FIGS. 10 and 11 show the final position of the expansion bolt and the expanded femoral stem. In this respect it will be appreciated that it may be necessary to modify the bolt taper, the length of the bolt taper, and/or the shape of the smooth tapered portion of the expansion bolt in a manner consistent with the desired effect of controlled and reliable expansion of the femoral stem as previously stated. The final position of the expansion bolt may sit proud relative to the femoral stem, or it may sit recessed within the expansion hole, and this may depend to some extent upon how far the screw is advanced into the femoral stem and how much expansion is required.

Figure 12:
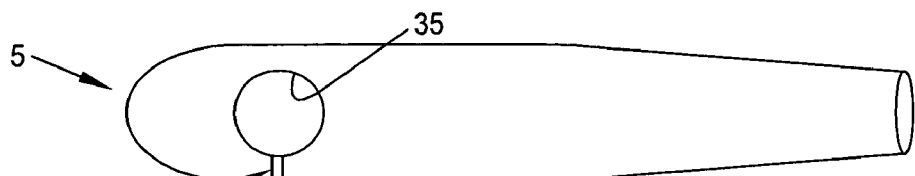
Figure 13:

As noted above, the longitudinally-extending sagittal slit 25 preferably extends across the entire anterior-to-posterior dimension of the implant. Alternatively, the longitudinally-extending sagittal slit 25 may extend only part way across the implant, e.g., from the anterior surface of the implant to the expansion hole (FIG. 12), or from the posterior surface of the implant to the expansion hole (FIG. 13).

Figure 14:
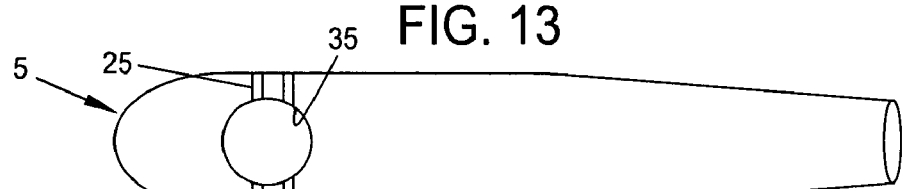

And/or the longitudinally-extending sagittal slit 25 may be replaced by a plurality of parallel longitudinally-extending sagittal slits 25 (FIG. 14).

In one form of the present invention, the anterior-to-posterior slit 25 within femoral stem 10 (FIG. 3), otherwise understood to be a sagittal slit, can also be combined with a medial-to-lateral ("coronal") slit 55 (FIG. 3) starting from the expansion hole and extending laterally. See, for example, FIG. 3, where such a coronal slit 55 is shown in phantom. The provision of both the sagittal slit 25 and the coronal slit 55 allows for expansion in both a medial-to-lateral direction and in an anterior-to-posterior direction and may aid in achieving press-fit stability.

The longitudinally-extending coronal slit 55 may extend medially of the expansion hole, or laterally of the expansion hole, or both.

Figure 15:
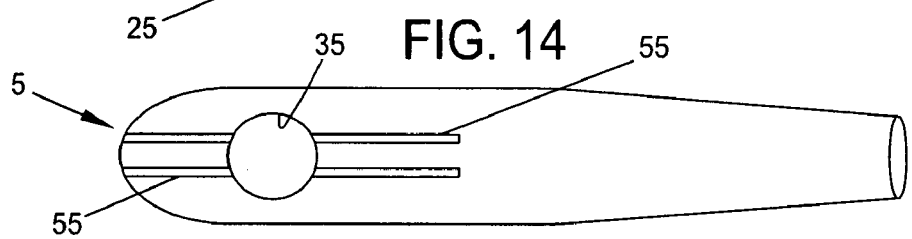

And/or the longitudinally-extending coronal slit 55 may be replaced by a plurality of parallel longitudinally-extending coronal slits 55 (FIG. 15).

Figure 16:
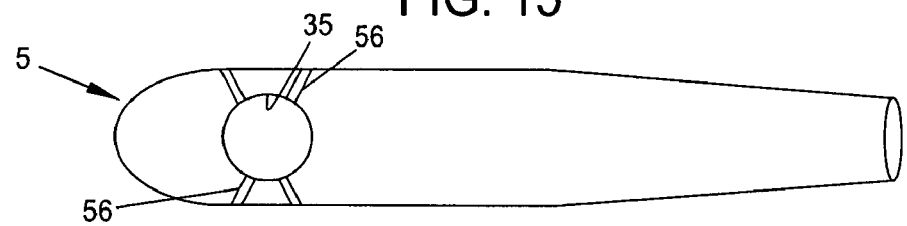
Figure 17:
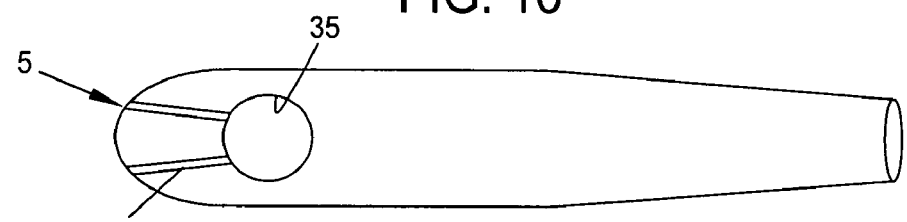
Figure 17A:
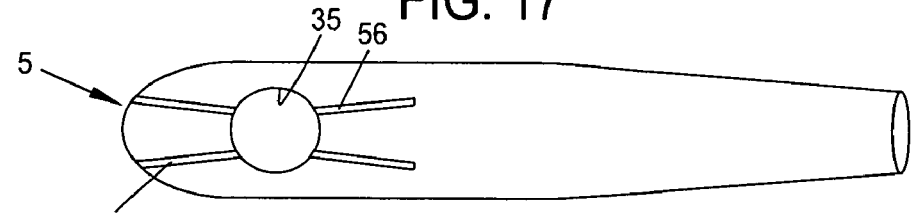

In one preferred construction, the aforementioned longitudinally-extending sagittal slit 25 and the aforementioned coronal slit 55 are replaced by one or more longitudinally-extending slits 56 that extend at a non-perpendicular angle to both the sagittal plane and the coronal plane. See FIGS. 16, 17 and 17A.

Figure 18:
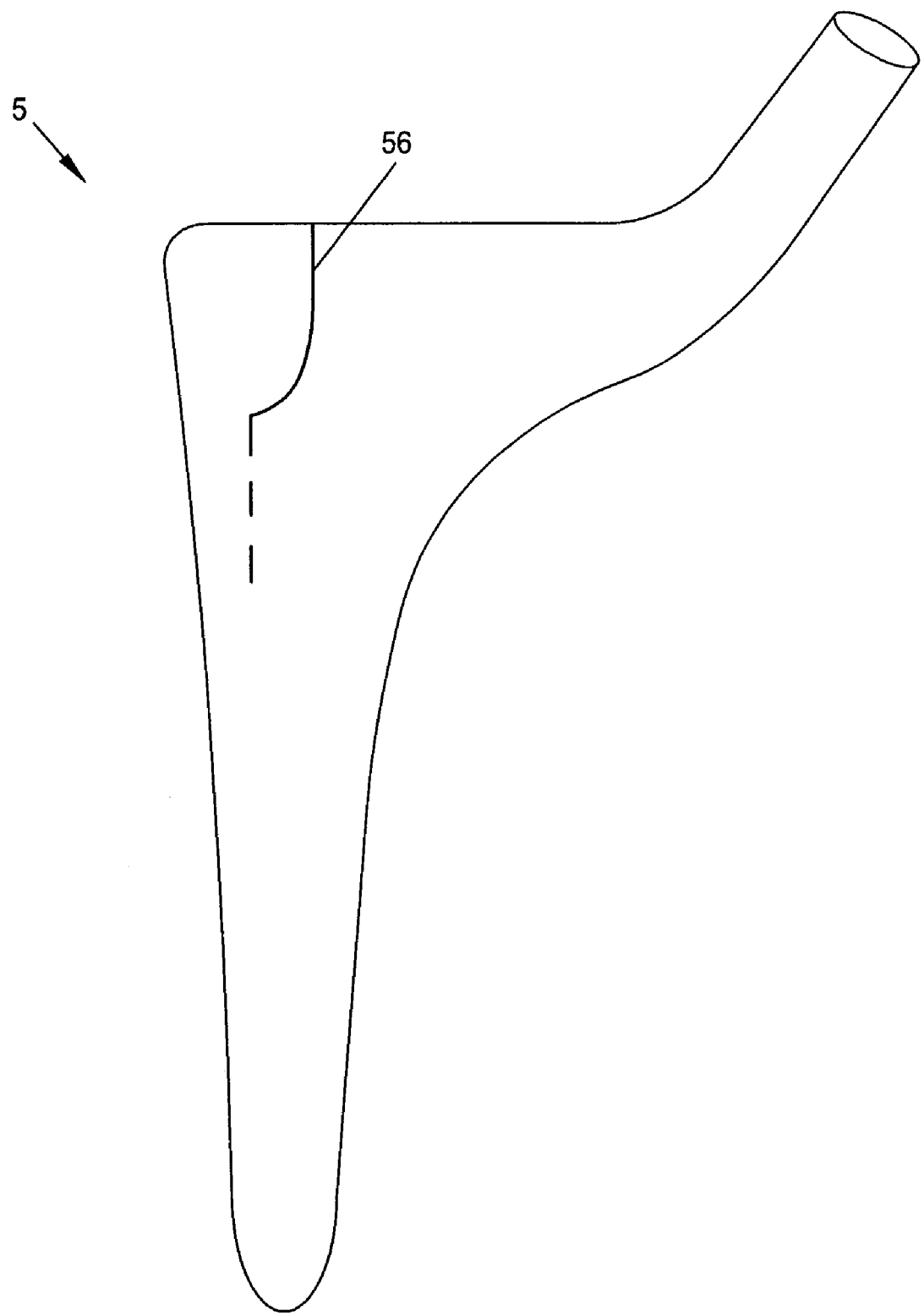

The longitudinally-extending slits may also take on more complex geometric configurations, e.g., they may start in the sagittal plane and migrate laterally as they extend distally so as to end in the coronal plane—this three-dimensional shift relative to proximal/distal location can provide a large surface area for expansion while minimizing the risk of implant or bone failure along the length of the longitudinally-extending slit. See the longitudinally-extending slit 56 shown in FIG. 18.

Additional slit configurations, which will be apparent to those skilled in the art in view of the present disclosure, may be utilized in order facilitate incrementally controlled expansion of the femoral stem.

Figure 19:
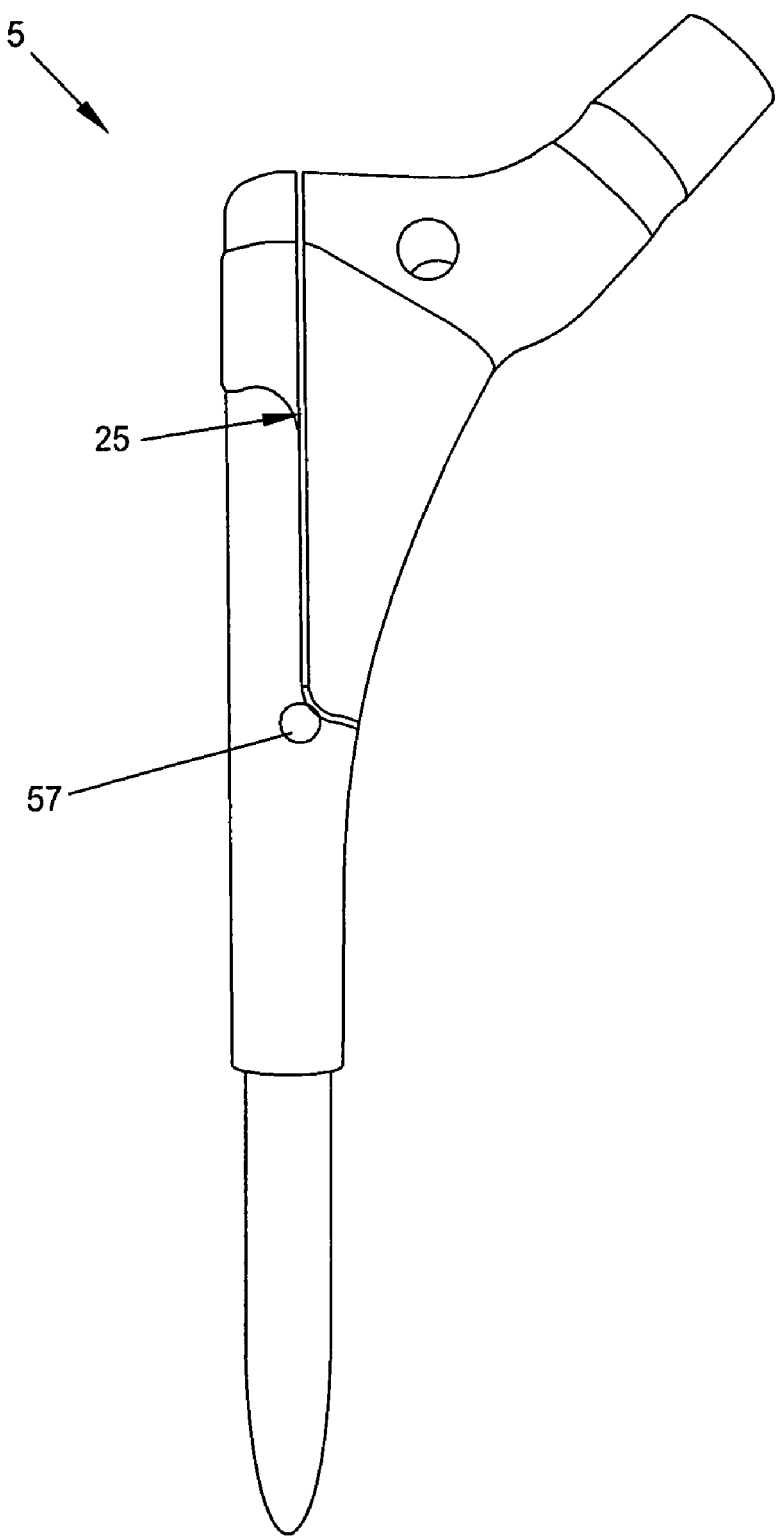

The distal aspect of the sagittal slit 25 and/or coronal slit 55 may end abruptly, or may end in a tapered or graduated manner, or may end in an unequal or asymmetric manner, with the anterior aspect of a slit ending at a different longitudinal position than the posterior aspect of a slit, etc. The terminal or distal extent of a slit may end in another geometrically configured manner and includes, but is not limited to, a circular hole, an oval or oblong shaped hole, or an otherwise rounded hole, the purpose of which is to minimize stress and implant fracture at this implant location, i.e., a "stress relief hole" or, more simply, a "relief hole". See the relief hole 57 shown in FIG. 19.

If desired, femoral stem 10 may include a collar, which is commonly defined as a prominence or extension along the medial aspect of the femoral stem, at the junction of the femoral stem's neck and the metaphyseal body. A collar typically rests upon the medial femoral bone known as the calcar, and serves to further protect against subsidence. Unlike prior designs where final press-fit stability is dependent upon sinking or advancing the stem further distally within the intramedullary canal, the present invention allows for post-implantation expansion of the femoral stem. Thus, the present invention serves to uncouple two previously linked goals, namely, the need for proper press-fit rotational stability and the need for proper and stable implant height. For this reason, incorporation of a medial collar does not prohibit final expansion and press-fit implantation and further protects against subsidence.

Preferred Manner of Use

In a preferred manner of use, the proximal femur is prepared in a customary manner typical of press-fit femoral stem preparation, often involving reaming, broaching, or a combination of the two surgical procedures. This is implant-specific and is understood by those skilled in the art of the present invention.

Once the femoral preparation is complete and the appropriate size of femoral implant 5 is selected, femoral stem 10 is inserted (using a conventional implant insertion tool, not shown) via mallet strikes in a manner consistent with standard insertion techniques. This technique is understood by those skilled in the art of the present invention.

Once the implant has reached proper position, indicated by the resting of the collar on the calcar, by comparison of the implant position to that of the previously used trial component, or any other method, instrument, or approach typically employed by the those skilled in the art of the invention, the aforementioned insertion tool (not shown) is removed or uncoupled from the femoral implant and expansion bolt 40 is introduced into expansion hole 35 (see FIG. 7).

Expansion bolt 40 is threaded into expansion hole 35 in a typical clockwise manner and advanced using expansion driver 53 (FIGS. 7-11) until such time that a desirable amount of expansion is achieved or until such time that sufficient internal hoop stresses are created between the implant and the surrounding bone.

Expansion Driver

Expansion driver 53 (FIGS. 7-11) can be designed as a torque driver with a pre-set limit to prevent over-expansion and to prevent the generation of excessive internal hoop stresses. Alternatively, it can be linked to a force meter whereby inherent resistance to advancement can be measured for and resistance from surrounding bone can be determined. The spirit of the instrument and the system is understood to be a means whereby excessive force generation is prevented while incrementally and reproducibly applying post-implant press-fit stability via implant expansion.

Locking Set Screw

Figure 20:
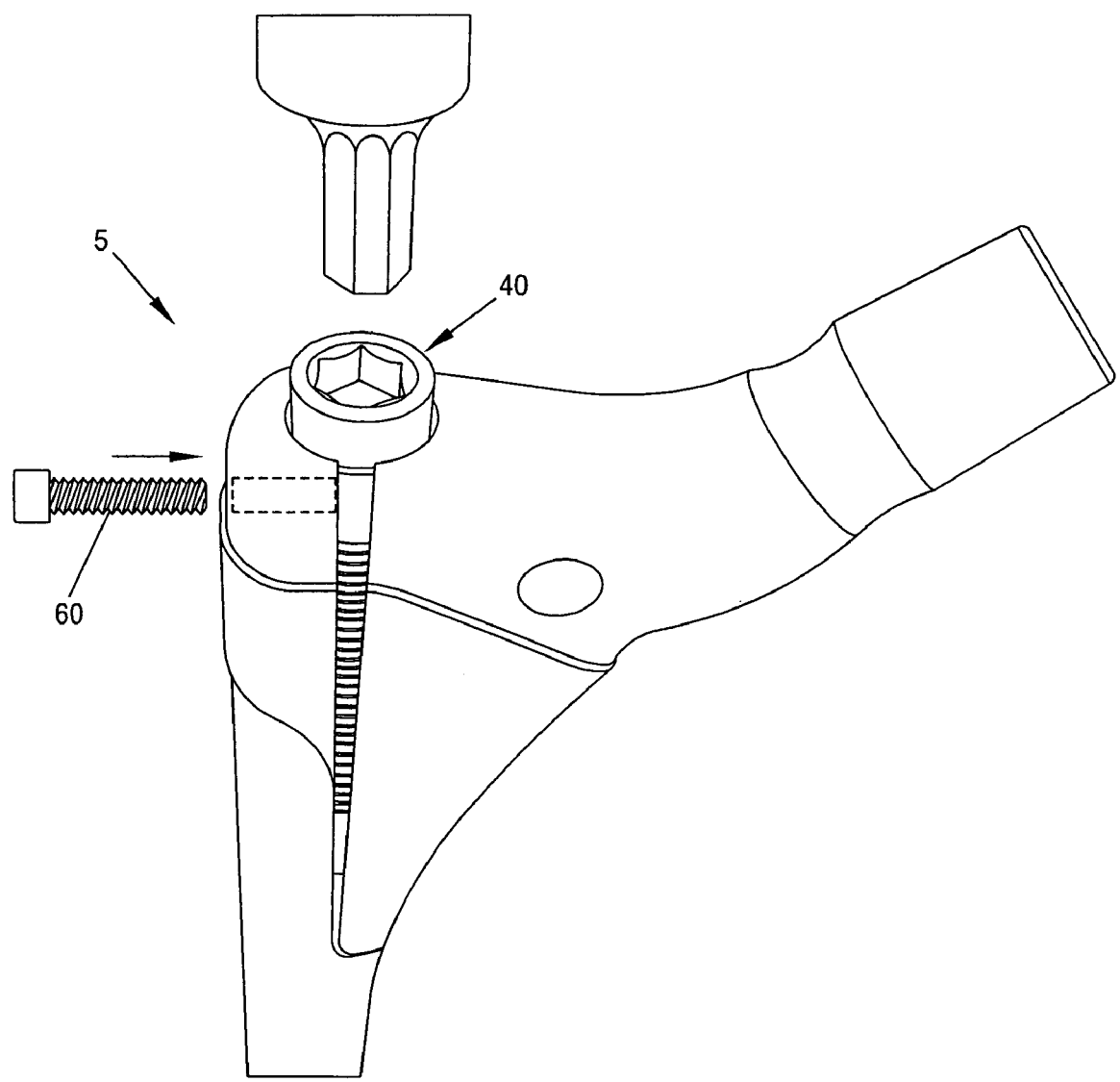

If desired, the present invention may also include a locking set screw 60 (FIG. 20) to prevent or protect against backing-out or loosening of the expansion bolt. Locking set screw 60 is intended to pass through a bore (not shown) in femoral stem 10 and engage expansion bolt 40 so as to lock the expansion bolt in position.

Neutralization Bar

The present invention further provides for the incorporation of a neutralization (or "locking") device (e.g., a cap or bar or screw, etc.) the purpose of which is to offset or neutralize forces passed across the slit (or slits) and measured at a variable level medial to the slit. The neutralization (or "locking") device (e.g., cap, bar or screw, etc.) is intended to engage the proximal aspect of the femoral stem in a manner which crosses the longitudinally-extending slit and which serves to bridge the more medial aspect and the more lateral aspect of the proximal femoral stem with the intent to limit or neutralize bending and stress at the most distal extent of the longitudinally-extending slit. See, for example, FIGS. 21-23, which show a neutralization (or "locking") device in the form of a cap 63 which engages lips 64 which are formed on the proximal end of the implant so as to hold the implant from expanding further about the longitudinally-extending slit. In this form of the invention, a cap of appropriate size is selected (e.g., from a kit having a range of differently-sized caps) after the implant has been expanded to the desired size, and then the selected cap is fit onto lips 64 so as to hold the implant in its desired configuration.

Advantages of the Present Invention

The present invention overcomes the limitations of previously designed press-fit femoral stems in that it uncouples (i) the implant position or height from (ii) implant stability. Prior femoral press-fit stem designs dictate that if rotational or axial stability is lacking, the implant must be impacted further distally into the intramedullary canal. The present invention permits rotational or axial stability to be improved simply by laterally expanding the implant, without requiring further distal movement of the implant. Furthermore, the only means for currently testing whether final implant position affords stability is to apply further force to the insertion handle via mallet strikes. This approach can, on occasion, result in an inadvertent femoral fracture. The current invention allows for optimal implant height or positioning within the femoral canal via standard implantation techniques, followed by post-implantation femoral stem expansion, resulting in appropriate pressurization of the proximal femur, generation of increased hoop stresses, and in turn increased press-fit stability of the femoral stem, independent of other considerations.

Additional Aspects of the Present Invention

Thus it will be appreciated that the present invention provides a femoral prosthesis for hip replacement surgery, wherein the femoral prosthesis comprises a femoral stem which comprises at least one slit opening on the proximal end of the femoral stem and extending longitudinally down the femoral stem. An expansion element is provided for wedging open the slit and laterally expanding the femoral stem after implantation in the femur. As a result of this construction, the femoral stem can be advanced longitudinally into the femur so that it assumes a desired longitudinal position within the femur, and then the expansion element can be used to wedge open the slit, and hence laterally expand the femoral stem, to an appropriate degree, whereby to apply the optimal amount of hoop-stress to the host bone. Significantly, this hoop-stress is applied about the proximal end of the femoral stem, where it can engage the adjacent metaphyseal bone of the proximal femur and provide secure fixation of the femoral stem to the host bone with minimal stress shielding.

In one preferred form of the invention, the femoral stem comprises a bore opening on the proximal end of the femoral stem and extending longitudinally therealong, with the at least one slit intersecting the bore. In one preferred form of the invention, the expansion element comprises a screw. One or both of the bore and screw are tapered, whereby longitudinal movement of the screw within the bore applies lateral forces to either side of the at least one slit, whereby to laterally expand the femoral stem.

Application to Other Joints

It should be appreciated that the novel OPS™ system of the present invention may be used in prosthetic components for other joints in the body (e.g., the shoulder, the knee, etc.), and/or for fracture fixation devices used throughout the body. By way of example but not limitation, the invention may be used to form a humeral prosthesis for the proximal humerus.

MODIFICATIONS

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A prosthesis comprising an elongated stem for disposition within a cavity formed in a bone, the elongated stem comprising:
   a distal end terminating in a distal end surface, a proximal end terminating in a proximal end surface and a longitudinal axis extending between the distal end and the proximal end;
   at least one longitudinally-extending slit extending distally from the proximal end surface and terminating intermediate the elongated stem;
   a longitudinally-extending threaded expansion hole extending distally from the proximal end surface and terminating intermediate the elongated stem; and
   an expansion bolt comprising a proximal end and a distal end and sized to be received within the threaded expansion hole;
   wherein the threaded expansion hole communicates with the at least one slit, and further wherein advancement of the expansion bolt within the threaded expansion hole results in incremental controlled lateral expansion of the longitudinal axis, whereby to secure the prosthesis within the cavity by means of a press-fit with the surrounding bone.

2. A prosthesis according to claim 1 wherein the at least one slit comprises a proximal end and a distal end.

3. A prosthesis according to claim 2 wherein the at least one slit creates a hinge point for the prosthesis adjacent to the distal end of the at least one slit.

4. A prosthesis according to claim 2 wherein the at least one slit terminates in a relief hole at its distal end, the relief hole configured to deliver stress over a larger area.

5. A prosthesis according to claim 2, further comprising a locking element for disposition across the at least one longitudinally-extending slit so as to limit lateral expansion of the prosthesis.

6. A prosthesis according to claim 1 wherein the prosthesis comprises two slits.

7. A prosthesis according to claim 6 wherein the two longitudinally-extending slits extend perpendicular to one another.

8. A prosthesis according to claim 1 wherein the expansion hole is symmetrically centered over the at least one longitudinally-extending slit.

9. A prosthesis according to claim 1 wherein the expansion hole is asymmetrically centered over the at least one longitudinally-extending slit.

10. A prosthesis according to claim 1 wherein the expansion hole is tapered at its proximal end.

11. A prosthesis according to claim 1 wherein the expansion bolt is tapered at its proximal end.

12. A prosthesis according to claim 1 wherein the expansion bolt is threaded at its distal end.

13. A prosthesis according to claim 1 wherein the expansion hole is threaded at its distal end, the expansion bolt is threaded at its distal end, and further wherein at least one of the expansion hole and the expansion bolt is tapered at its proximal end.

14. A prosthesis according to claim 1, further comprising a locking set screw for extending through the prosthesis and engaging the expansion bolt.

15. A prosthesis according to claim 1 wherein the bone is the femur.

16. A prosthesis according to claim 1 wherein the bone is the femur, the prosthesis comprises at least one longitudinally-extending slit, and further wherein the longitudinally-extending slit extends in the sagittal plane.

17. A prosthesis according to claim 1 wherein the bone is the femur, and further wherein the at least one slit extends in the coronal plane.

18. A prosthesis according to claim 1 wherein the bone is the femur, the prosthesis comprises first and second longitudinally-extending slits, and further wherein the first longitudinally-extending slit extends in the sagittal plane and the second longitudinally-extending slit extends in the coronal plane.

19. A prosthesis according to claim 1 wherein the bone is the femur, and further wherein the slit extends at a non-perpendicular angle to the sagittal plane and at a non-perpendicular angle to the coronal plane.

20. An inserter for inserting the prosthesis of claim 1 in the cavity, wherein the inserter comprises an elongated shaft comprising a proximal end and a distal end and being sized to be received within the expansion hole, the elongated shaft being threaded at its distal end so as to selectively engage the threads at the distal end of the expansion hole.

21. An inserter according to claim 20 wherein the proximal end of the inserter is adapted to receive mallet strikes so as to insert the prosthesis into the cavity.

22. An expansion driver for advancing the expansion bolt of the prosthesis of claim 1, wherein the expansion driver includes means for limiting the force applied to the expansion bolt by the expansion driver.

23. An expansion driver for advancing the expansion bolt of the prosthesis of claim 1, wherein the expansion driver includes means for determining the force applied to the expansion bolt by the expansion driver.

* * * * *